(12) United States Patent
Livingston et al.

(10) Patent No.: US 7,931,021 B2
(45) Date of Patent: Apr. 26, 2011

(54) SUPPORT DEVICE FOR RESPIRATORY INTERFACE

(75) Inventors: Mitchell Andrew Livingston, Stittsville (CA); Stephen Keir Roberts, Ottawa (CA)

(73) Assignee: BRAEBON Medical Corporation, Kanata (CA)

( * ) Notice: Subject to any disclaimer, the term of this patent is extended or adjusted under 35 U.S.C. 154(b) by 757 days.

(21) Appl. No.: 11/691,104

(22) Filed: Mar. 26, 2007

(65) Prior Publication Data

US 2008/0236588 A1    Oct. 2, 2008

(51) Int. Cl.
*A62B 9/04*    (2006.01)
*F16L 3/00*    (2006.01)

(52) U.S. Cl. ......... 128/200.24; 128/204.18; 128/206.21; 128/206.24; 128/206.27; 248/75; 248/121

(58) Field of Classification Search ............. 128/200.24, 128/204.18, 207.11, 201.22, 201.23, 202.18, 128/202.27, 205.25, 206.21, 206.27, 845; 248/75, 125.8, 121, 122.1, 123.11, 123.2, 248/106, 280.11, 292.11
See application file for complete search history.

(56) References Cited

U.S. PATENT DOCUMENTS

| | | | |
|---|---|---|---|
| 2,963,247 A * | 12/1960 | Collier et al. .................. | 248/81 |
| 3,464,411 A * | 9/1969 | Martinez .................. | 128/202.18 |
| 3,482,571 A * | 12/1969 | Behrendt .................. | 128/202.18 |
| 4,020,834 A * | 5/1977 | Bird .......................... | 128/204.25 |
| 4,321,917 A * | 3/1982 | Campbell ................. | 128/205.26 |
| 4,593,688 A * | 6/1986 | Payton .................... | 128/200.28 |
| 4,838,258 A * | 6/1989 | Dryden et al. ............ | 128/204.18 |
| 5,279,486 A | 1/1994 | Harmon | |
| 6,119,693 A | 9/2000 | Kwok et al. | |
| 6,224,027 B1 * | 5/2001 | Johnson et al. ............ | 248/125.8 |
| 6,347,631 B1 | 2/2002 | Hansen et al. | |
| 6,470,886 B1 | 10/2002 | Jestrabek-Hart | |
| 6,516,802 B2 | 2/2003 | Hansen et al. | |
| 6,520,182 B1 | 2/2003 | Gunaratnam | |
| 6,629,532 B2 | 10/2003 | Campbell, Sr. | |
| 6,679,261 B2 | 1/2004 | Lithgow et al. | |
| 6,691,708 B2 | 2/2004 | Kwok et al. | |
| 6,776,161 B2 | 8/2004 | Horn | |
| 6,805,117 B1 | 10/2004 | Ho et al. | |
| 6,854,465 B2 | 2/2005 | Bordewick et al. | |
| 6,871,649 B2 | 3/2005 | Kwok et al. | |
| 6,899,102 B1 | 5/2005 | McGlothen | |
| 6,907,882 B2 | 6/2005 | Ging et al. | |
| 6,926,004 B2 | 8/2005 | Schumacher | |
| 6,973,929 B2 | 12/2005 | Gunaratnam | |
| 6,997,188 B2 | 2/2006 | Kwok et al. | |
| 7,004,170 B1 | 2/2006 | Gillstrom | |
| 7,011,087 B1 * | 3/2006 | Sullivan .................... | 128/200.24 |

(Continued)

*Primary Examiner* — Justine R Yu
*Assistant Examiner* — LaToya M Louis
(74) *Attorney, Agent, or Firm* — Mukundan Chakrapani; Borden Ladner Gervais LLP

(57) ABSTRACT

A patient interface support that supports a patient interface of a PAP device and generates a pre-selected engagement pressure at the patient interface to create a seal between the patient interface and the patient's airflow passages when the interface support is in use while alleviating the strain on the patient's head. The patient interface support includes a base for attachment to a support surface; and, a support extension having a joint; a patient interface mount; and, biasing means. The joint movably connects the support extension to the base, the patient interface mount supports the patient interface, and the biasing means generates a pre-selected engagement pressure at the patient interface to create a seal between said patient interface and the patient's airflow passages when said interface support is in use.

15 Claims, 10 Drawing Sheets

U.S. PATENT DOCUMENTS

| | | |
|---|---|---|
| 7,021,312 B2 | 4/2006 | Cannon |
| 7,040,581 B2 | 5/2006 | Noelke et al. |
| 7,047,971 B2 | 5/2006 | Ho et al. |
| 7,047,972 B2 | 5/2006 | Ging et al. |
| 7,066,179 B2 | 6/2006 | Eaton et al. |
| 7,089,941 B2 | 8/2006 | Bordewick et al. |
| 7,096,867 B2 | 8/2006 | Smith et al. |
| 7,124,755 B2 | 10/2006 | Van Hooser |
| 7,146,976 B2 | 12/2006 | McKown |
| 7,152,602 B2 | 12/2006 | Bateman et al. |
| 7,178,528 B2 | 2/2007 | Lau et al. |
| 7,448,376 B2 * | 11/2008 | Lepel ................. 128/200.14 |
| 7,513,252 B2 * | 4/2009 | Berg .................. 128/203.12 |
| 2002/0117177 A1 | 8/2002 | Kwok |
| 2002/0148473 A1 | 10/2002 | Kwok et al. |
| 2004/0060561 A1 | 4/2004 | Kwok et al. |
| 2005/0103342 A1 * | 5/2005 | Jorczak et al. ......... 128/205.24 |
| 2005/0139219 A1 | 6/2005 | Gunaratnam |
| 2005/0173599 A1 | 8/2005 | Noelke et al. |
| 2005/0211252 A1 | 9/2005 | Lang et al. |
| 2006/0005840 A1 | 1/2006 | Cannon |
| 2006/0032504 A1 | 2/2006 | Burton et al. |
| 2006/0081252 A1 | 4/2006 | Wood |
| 2006/0118119 A1 | 6/2006 | Berthon-Jones et al. |
| 2006/0191539 A1 | 8/2006 | Ho et al. |
| 2006/0201506 A1 * | 9/2006 | Makinson et al. ....... 128/204.21 |
| 2006/0213521 A1 | 9/2006 | Radney |
| 2006/0266362 A1 | 11/2006 | Smith et al. |
| 2006/0278233 A1 | 12/2006 | McAuley et al. |
| 2006/0283456 A1 | 12/2006 | Geiselhart et al. |
| 2006/0283457 A1 | 12/2006 | Woodard et al. |
| 2006/0283459 A1 | 12/2006 | Geiselhart et al. |
| 2006/0283460 A1 | 12/2006 | Brown et al. |
| 2006/0283461 A1 | 12/2006 | Lubke et al. |
| 2006/0289010 A1 | 12/2006 | Kwok et al. |
| 2007/0000495 A1 | 1/2007 | Matula, Jr. et al. |
| 2007/0017525 A1 | 1/2007 | Madaus et al. |
| 2007/0045481 A1 | 3/2007 | Adams |
| 2008/0078397 A1 * | 4/2008 | Scott et al. ............. 128/205.25 |

* cited by examiner

SUPPORT DEVICE FOR RESPIRATORY INTERFACE

FIELD OF THE INVENTION

The present invention relates generally to a device for supporting a patient interface of an airway gas-delivery system or apparatus. In particular, the present invention relates to a device for supporting the interface of positive airway pressure device used for treatment of obstructive sleep apnea.

BACKGROUND OF THE INVENTION

Obstructive sleep apnea (OSA) is a condition that affects an estimated 14 million Americans. The condition is caused by relaxation of soft tissue in the upper airway during sleep, resulting in its obstruction. OSA is characterized by a complete cessation of breathing during sleep for 10 or more seconds (apnea), or a reduction in breathing for 10 or more seconds causing a 4% or greater decrease in blood oxygen level (hypopnea). Individuals having 5 or more apneic or hypopneic events per hour are diagnosed as suffering from OSA. The obvious side effects of sleep apnea are daytime sleepiness and chronic fatigue. However, OSA is known to be a contributing factor in hypertension, heart disease, as well as other serious health conditions.

The most common treatment for obstructive sleep apnea (OSA) is positive pressure (above-ambient) applied at the patient's nose or mouth, or at both the nose and mouth. This treatment is also frequently prescribed to patients suffering from chronic obstructive pulmonary disease (COPD). FIG. 1 is a schematic diagram of an apparatus conventionally used in positive airway pressure (PAP) therapy treatment. The PAP device 120 supplies pressurized atmospheric air, which is conveyed through a hose 122 to a patient interface 124, adapted to deliver the pressurized air to the patient airway through either the nares 106, the mouth 108, or both the nares 106 and the mouth 108. The positive air pressure helps prevent obstruction of the patient airway. Treatment pressures typically range between 4 and 20 cm $H_2O$ for OSA, and up to 35 cm $H_2O$ for COPD, depending primarily on the severity of the condition.

Positive airway pressure devices 120 often also include other components or features that are adapted to increase patient comfort, or which may be used for diagnostic purposes. Examples include humidification of the treatment air to prevent dryness and soreness of the nose, mouth, and airway; filters designed to remove irritants and allergens from the treatment air; and, diagnostic recording instruments. It is, therefore, understood that a PAP device, in the current context, may also comprise any such additional features, wherein the primary medical function of the device is to supply pressurized air to the patient airway.

In order for positive airway pressure treatment to be effective, a mechanism for maintaining the patient interface 124 securely in position is required (not shown in FIG. 1). This requirement maintains a seal between the patient interface 124, and the nares 106 and/or mouth 108 of the patient, without which loss of applied pressure results, due to leaks in the system. Interface leaks can also cause arousal, either from the sensation of airflow on the face, or because of the sound generated by the increased airflow.

FIGS. 2a and 2b show, schematically, the principle of the most common type of support device for a respiratory interface. The apparatus consists of a frame 130, typically made of rigid plastic material, to which the interface 124 is attached, or into which it is integrated. One end of the interface 124 is formed to be suitable for delivering the treatment air to the nares 106 (FIG. 2a) or to the nares 106 and mouth 108 (FIG. 2b) of the patient. The other end of the interface 124 is adapted to receive pressurized air, supplied by the PAP device 120 through a length of hose or tubing 122. Elastic straps 132, or other similar mechanisms, are fixed around the head 102 of the patient, thus securing the frame 130 of the apparatus to the head 102 of the patient.

Ideally, in order to provide a proper seal between the interface and the patient, light pressure should be applied on the interface 124, in the direction toward the nares 106 and/or mouth 108 of the patient. With the apparatus shown in FIGS. 2a and 2b, the force opposing the sealing force is applied to the head 102 of the patient, through the frame 130 and/or straps 132 of the device. Since the nose and the skin of the scalp 102a are pliable, relatively minor movement or facial deformation of the patient may break the seal during sleep, or by the hose 122 tugging on the frame 130 or interface 124 of the apparatus.

To overcome the problem of sealing, various modifications and improvements to this type of interface support device have been devised (e.g. U.S. patent applications 2007/0017525 A1, 2006/0081252 A1, and 2006/118119 A1). These improvements typically involve means of more tightly securing the apparatus to the head 102 of the patient, by means of additional head-straps 132 or chin-straps 132a (FIG. 2c), as taught for example in U.S. patent application 2006/0283461 A1, and U.S. Pat. Nos. 6,470,886 B1, 7,047,971 B2, and 6,926,004 B2. The length, and therefore tension, of the straps 132 and 132a is also typically adjustable by the wearer by the use of hook-and-loop (Velcro™) fasteners, buckles, or any number of similar fasteners. While more rigidly fixing the support device to the head 102 of the patient, such measures result in additional pressure applied to the head 102 of the patient, which do not contribute directly to maintaining sealing pressure between the interface 124 and the patient. Prolonged use can result in mild headache or other discomfort, and may also leave marks or lines on head and face where the frame and/or straps contact the patient wearing the device. To alleviate this discomfort, the thickness of cushioning materials added to the areas contacting the patient is increased. However, the foam or gel materials typically used represent an additional layer of pliable material, which in turn requires greater tension on the straps, and increased pressure on the cranium.

In FIGS. 2a and 2b, the attachment 130a on the frame 130 of the device provided for the hose 122 is shown pointing substantially upward, and is located above the interface 124. However, in different embodiments of these prior-art inventions the hose 122 may approach the interface from the front, from below, or from one side of the interface 124.

Alternative measures for improving the sealing capability of interface support devices allow for manual adjustment of the position of the interface 124 relative to the frame 130. Examples, such as those taught in U.S. patent applications 2006/0213521 A1, 2006/0191539 A1, 2006/0032504 A1, and 2004/0060561 A1, include: plastically deformable elements such as pieces of wire, hinged joints, ball joints, and lead screws. Various means are used to maintain the position of these parts once adjusted, including mechanisms such as lock-tabs, snap-hooks, thumbscrews, or friction caused by close fit or slight interference between parts. Another invention uses flexible members as part of the frame 130 to provide some degree of automatic positional adjustment (e.g. U.S. Pat. No. 6,854,465 B2). Other inventions providing varying degrees of automatic positional adjustment, or a range of motion between the frame of the device and the interface, are provided in U.S. Pat. No. 7,096,867 B2, and U.S. patent applications 2006/0283456 A1 and 2006/0238459 A1. In yet another alternative (e.g. U.S. Pat. Nos. 6,347,631 B1 and 6,516,802 B2, and U.S. patent application 2002/0117177 A1), the frame is fitted to the occipital crown 102b of the patient, which eliminates, or at least reduces, the need for tensioning straps. However, in each of the above inventions, the primary solution is to restrain the motion of the frame by fixing it to a part of the head of the patient, thus placing strain on the head.

Still other devices (e.g. U.S. Pat. No. 7,066,179 B2, and U.S. patent application 2006/0283457 A1) comprise a hinged or rotatable fitting, such that the air hose 122 may approach the interface 124 from virtually any direction.

Other medical conditions exist for which treatment comprises delivery of a gas to the airway of a patient, and for which a patient interface support device is required. Most commonly, the gas is oxygen, or oxygen-enriched air delivered to a patient suffering from disease or injury causing loss of respiratory function. As shown in FIG. 3, a gas is supplied from a pressure-vessel and conveyed, through a pressure or flow-regulating valve, along a length of hose or tubing 144 to a suitable patient interface, such as the nasal cannula 146 shown in FIG. 3. The cannula 146 is typically fixed to the patient by securing the tubing 144 behind the head 102, or under the chin 104 of the patient, as depicted in FIG. 3. Adhesive tape 148 may also be additionally used to secure the tubing to the face or cheeks of the patient. As can be seen from FIG. 3, the hose or tubing cab easily become entangled with the patient. U.S. Pat. Nos. 5,279,486 A; 7,040,581 B2; 7,124,755 B2; and, U.S. patent application 2007/0045481 A1 disclose various devices which provide support for the supply hose and improve patient comfort. These types of construction have generally been devised to reduce leaks and discomfort caused by the supply hose becoming tangled or caught in the patient, or other objects such as patient bedding.

An alternative arrangement for securing the patient interface to the head of the patient consists of a dental appliance, which is molded around the teeth of the patient, and fixed to the upper mandible during use, as disclosed in U.S. Pat. No. 7,021,312 B2. The frame extends outside the mouth of the patient, and a means for rigidly attaching the nasal interface to the frame is provided. Optionally, the invention also provides a passage for air to enter the mouth of the patient. This apparatus provides a more rigid base for attaching the frame of the interface support device than the moveable and pliable skin of the cranium. However, wearing a device inside the mouth can also be a source of discomfort for some patients, even when properly fitted. Furthermore, while the invention eliminates strain placed on the cranium, the sealing force is now applied to the jaw of the patient, which may result in further pain and discomfort.

Although effectiveness of positive airway pressure treatment is well proven, approximately half of patients prescribed PAP for treatment of obstructive sleep apnea do not use their device regularly. Discomfort, including that caused by interface support devices, and arousal due to interface leaks, are both known to be contributing factors in this lack of treatment compliance. Therefore, there is a need for support devices designed to improve patient comfort by addressing these issues, which in turn will increase patient compliance.

It is, therefore, desirable to provide a support device that alleviates the strain on the patient's head by supporting the patient interface device while at the same time maintaining a seal between the interface device and the patient's airflow passages.

SUMMARY OF THE INVENTION

It is an object of the present invention to obviate or mitigate at least one disadvantage of previous interface support devices. This is achieved by providing a patient interface support that supports a patient interface of a PAP device, and generates a pre-selected engagement pressure at the patient interface, to create a seal between the patient interface and the patient's airflow passages when the interface support is in use, while alleviating the strain on the patient's head.

In a first aspect, the present invention provides a patient interface support for a Positive Airway Pressure (PAP) device, the device including a pressurized air source, a patient interface for supplying air to a patient's airflow passages and an air supply conduit for supplying pressurized air from the pressurized air source to said patient interface. The patient interface support comprises: a base for attachment to a support surface; and, a support extension having a joint; a patient interface mount; and, biasing means. The joint moveably connects the support extension to the base, the patient interface mount supports the patient interface, and the biasing means generates a pre-selected engagement pressure at the patient interface to create a seal between the patient interface and the patient's airflow passages when the interface support is in use.

The support device of the present invention relieves discomfort arising from strain placed on the cranium and/or mandible of the patient. This is achieved by eliminating the elastic straps, or other similar mechanisms, used in prior art devices to secure the interface support mechanism to the head of the patient.

An embodiment of the present invention comprises a base, and a moveable support extension. The base is fastened securely at a first end to a fixed point on the bed of the patient, or another fixed location or object in the room. The second, free end, of the base, is ideally located near the crown of the head of the prostrated patient (i.e. toward the headboard). A first end of the moveable support extension is coupled to the free end of the base, and the second end of the moveable support extension contains a coupling adapted to attach to the patient interface. The moveable support extension comprises force-generating elements designed to provide sealing pressure between the interface and the patient. The base and moveable support extension are located away from the patient, such that only the sealing surface of the interface comes into contact with the patient. In the preferred embodiment of the present invention, the hose supplying pressurized air from the PAP device is connected to a point located on the base of the subject device, thus eliminating leaks and discomfort caused by tugging on the patient interface.

Several examples of means for providing the pressure necessary to maintain a seal between the interface and the patient, and for automatically tracking the motion of the patient, are provided in the various aspects and embodiments of the present invention. These embodiments involve the use of elastically deformable, as well as rigid members, through which tension is maintained.

In addition, various means are provided for fixing the base to a wall of the room, to the floor of the room, to the bed of the patient, or to the pillow of a patient.

Other aspects and features of the present invention will become apparent to those ordinarily skilled in the art upon review of the following description of specific embodiments in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

The present invention provides a patient interface support that supports a patient interface of a PAP device. The patient interface support also generates a pre-selected engagement pressure at the patient interface to create a seal between the patient interface and the patient's airflow passages when said interface support is in use while alleviating the strain on the patient's head.

Figure 1:
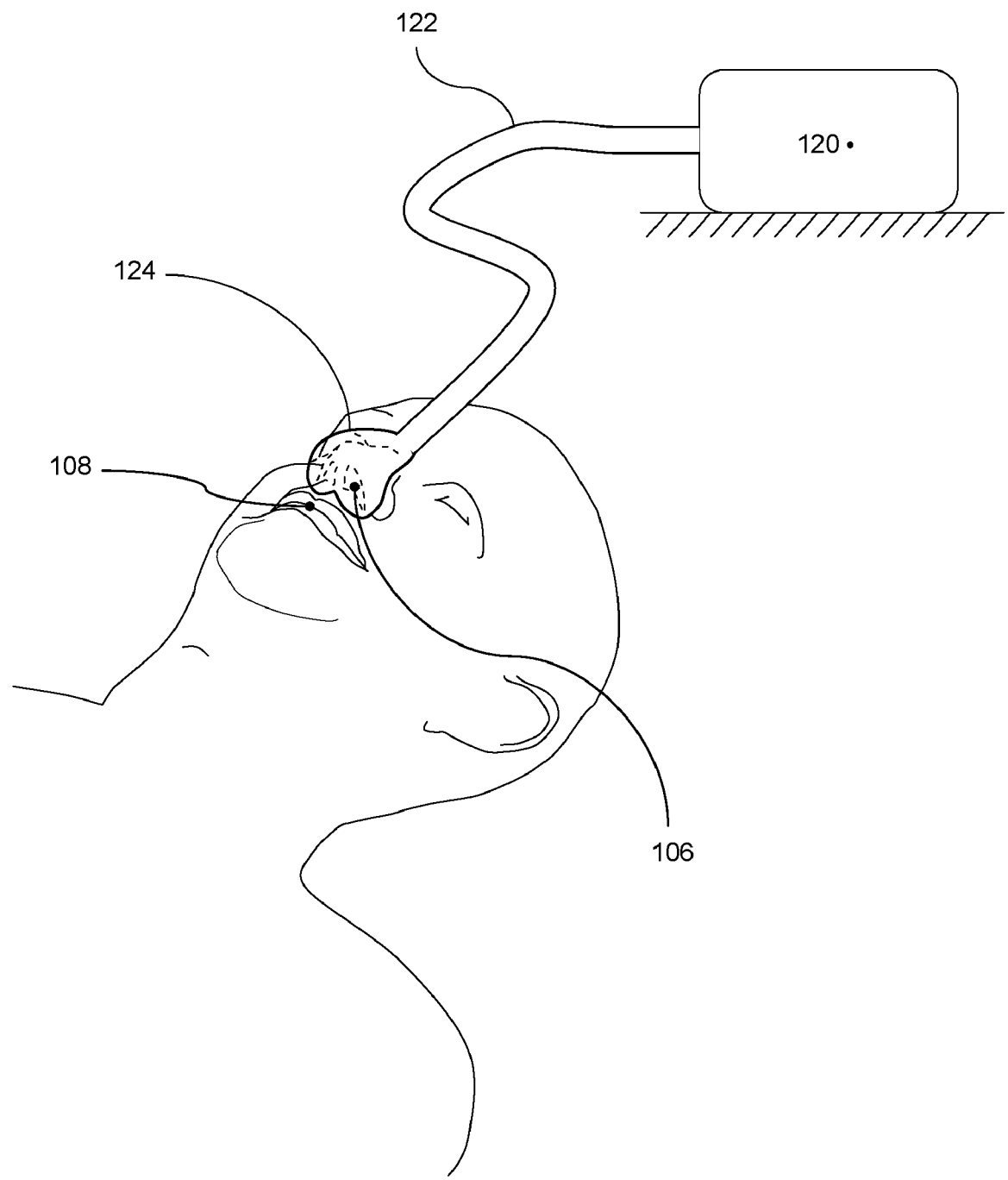
FIG. 1 depicts schematically a conventional apparatus used for positive airway pressure treatment.
Figure 2A:
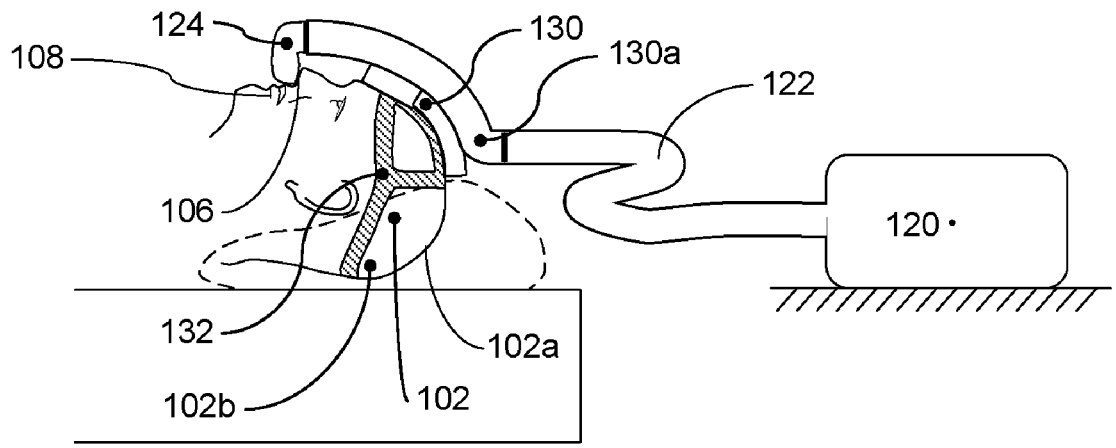
FIGS. 2a, 2b, and 2c depict examples of conventional prior art interface support devices.
Figure 2B:
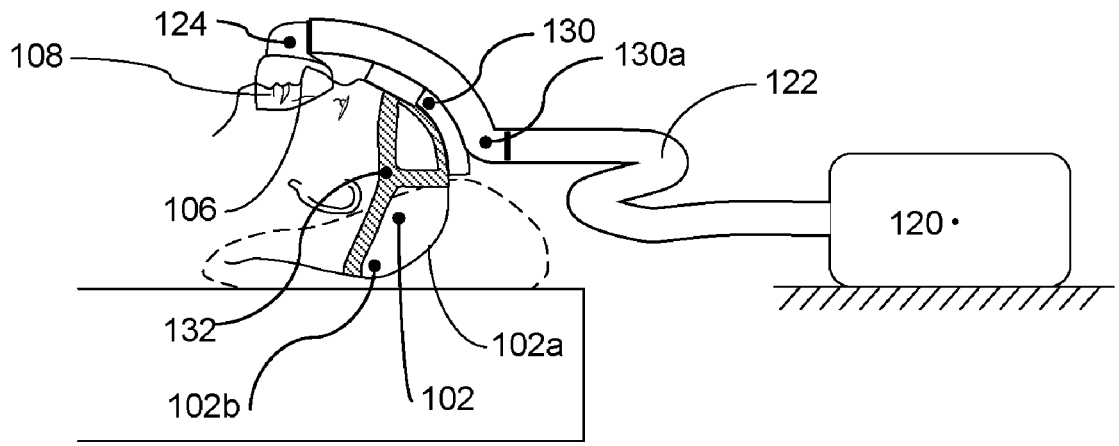
Figure 2C:
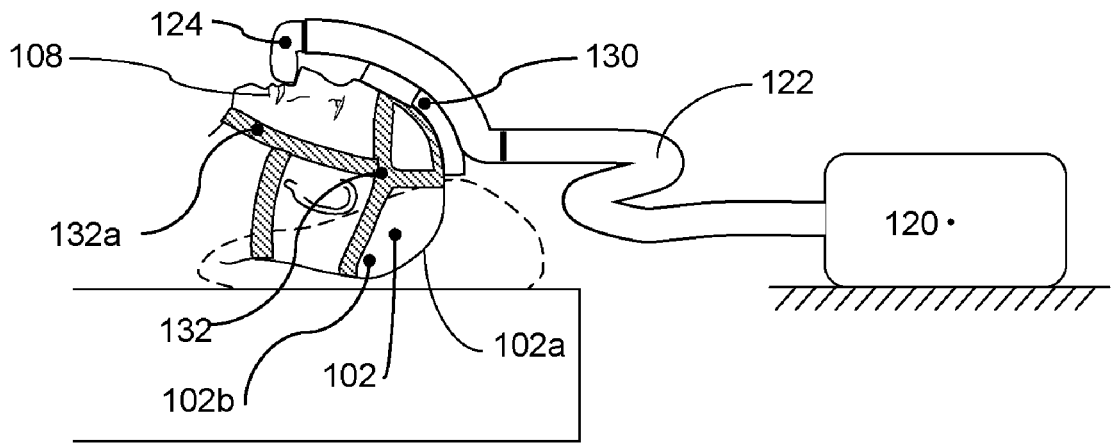
Figure 3:
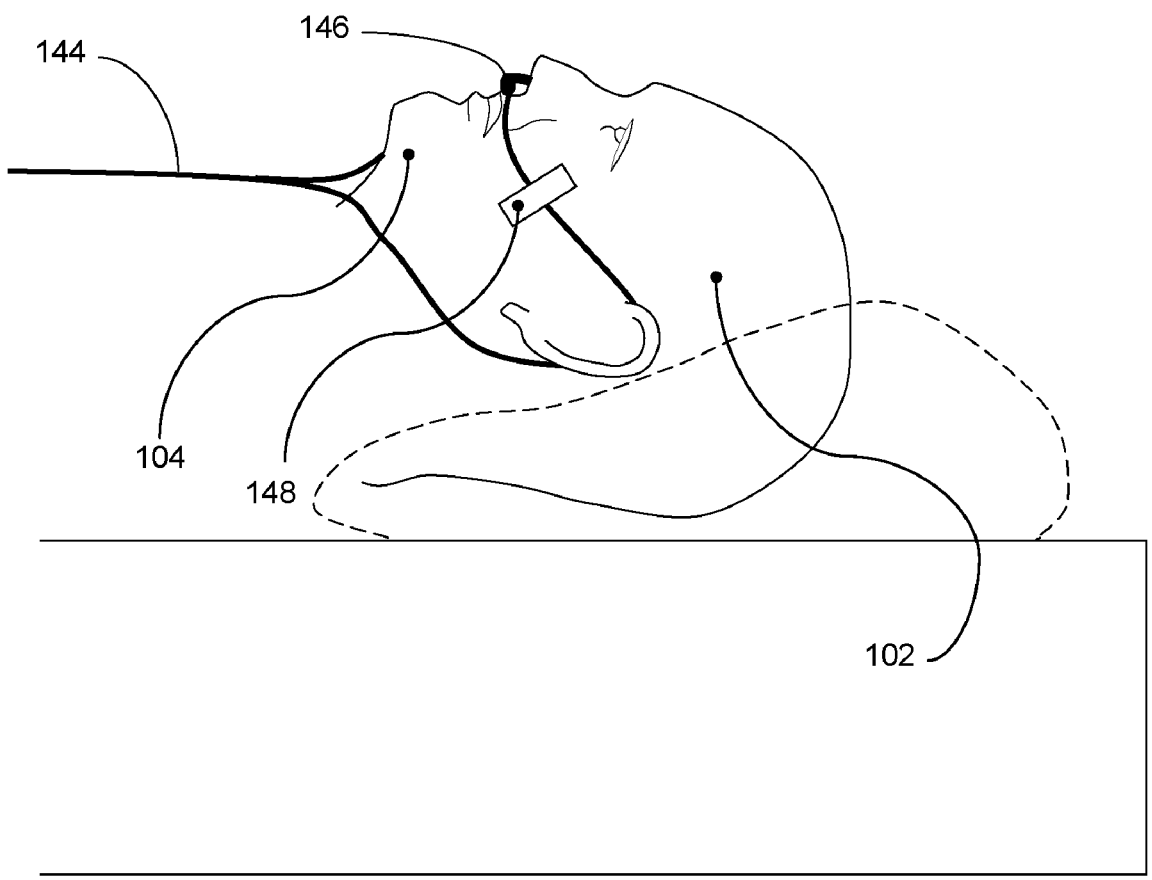
FIG. 3 depicts an example of conventional oxygen cannula support.
Figure 4:
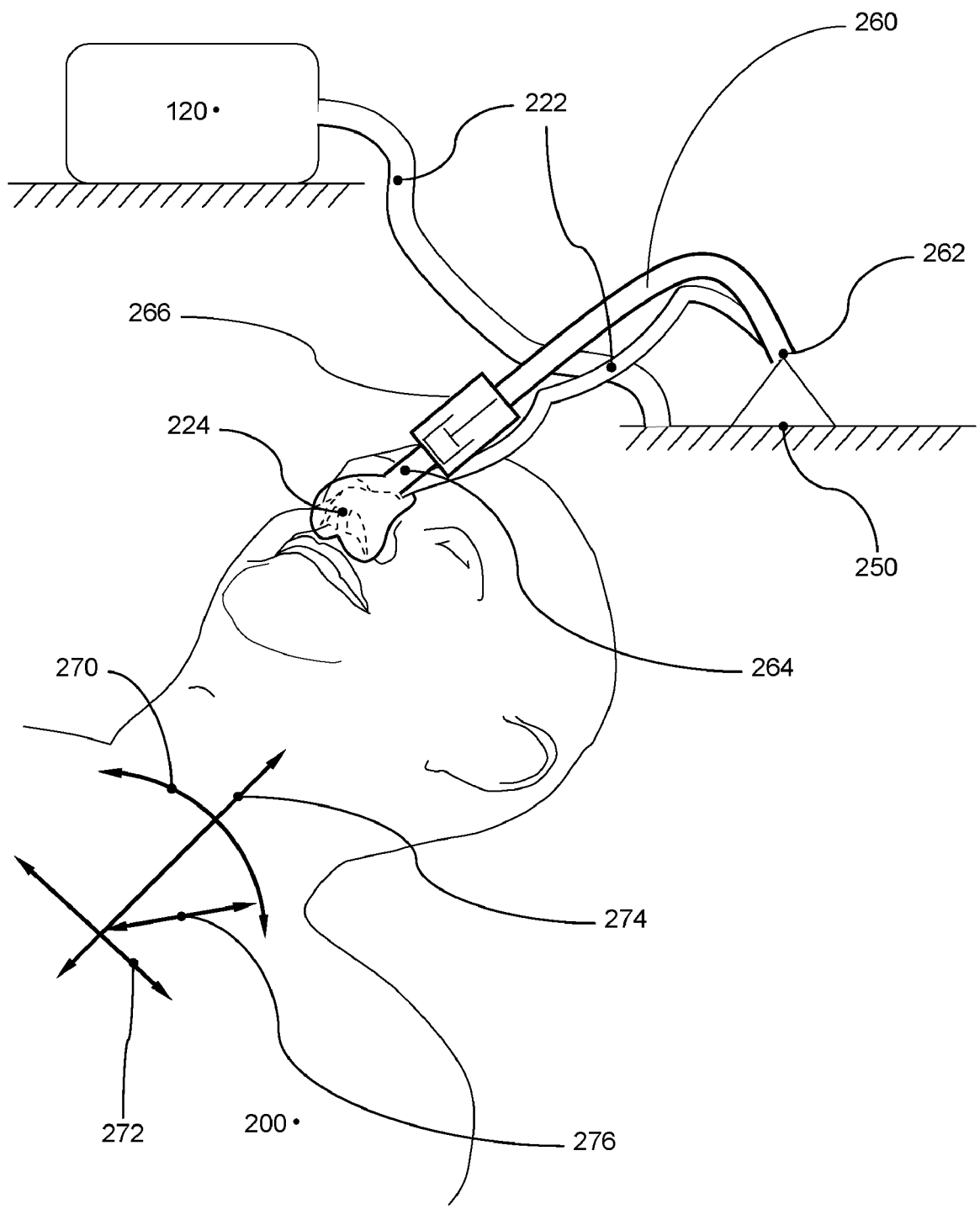
FIG. 4 shows schematically the principle of the present invention.

The principle of the support device according to the present invention is shown in FIG. 4. The patient interface support comprises of a base 250 for attachment to a support surface; and, a support extension 260 having a joint 262; a patient interface mount 264; and, biasing means 266. The joint 262 movably connects the support extension 260 to the base 250, the patient interface mount 264 supports the patient interface 224, and the biasing means 266 generates a pre-selected engagement pressure at the patient interface to create a seal between the patient interface 224 and the patient's airflow passages when the interface support is in use.

The base 250 provides a fixed location to which the support extension 260, and suitable air supply hose 222 of the PAP device 120 may be attached. The support extension 260 supports the patient interface 224 of the PAP device in such a way as to follow the motion of the patient wearing the device during sleep, while maintaining slight pressure at the contact surfaces between the patient and the interface 224. In the preferred embodiment of the present invention, the components of the device are arranged such that the only contact between the patient and any treatment apparatus is at the location where a seal is made between the interface 224 and the patient 200.

Motion of the support extension 260 is achieved through any of several means that are well known in the art. While it is not practical to allow for an unlimited range of motion of the patient, the largest ranges of motion of the patient are expected to be: i) rotation about the longitudinal axis of the patient (rolling); ii) lateral translation (sideways shifting); and iii) longitudinal translation (upward/downward shifting), respectively depicted by the arrows 270, 272, and 274, in FIG. 4. For future reference, it is noted that rolling motion followed by lateral translation of the patient (i and ii above) could equally well be described in terms of rolling motion 270 followed by a radial translation, depicted by the arrows 276, by a suitable transformation of the coordinate system. The mechanisms described in subsequent embodiments of the present invention are primarily designed to automatically track a patient moving through some or all of these three types of motion. However, it is recognized that other patient motions may occur, and that additional means, similar to those described herein, may also be used to track these other patient motions.

Pressure is maintained at the sealing surface between the patient and the interface by use of force-generating members that control the motion of the various components of the moveable support extension. These force-generating members are also selected from those well known in the art. The mechanics of implementing the above-mentioned motions and forces will become evident in the examples given in the subsequent embodiments.

Figure 5:
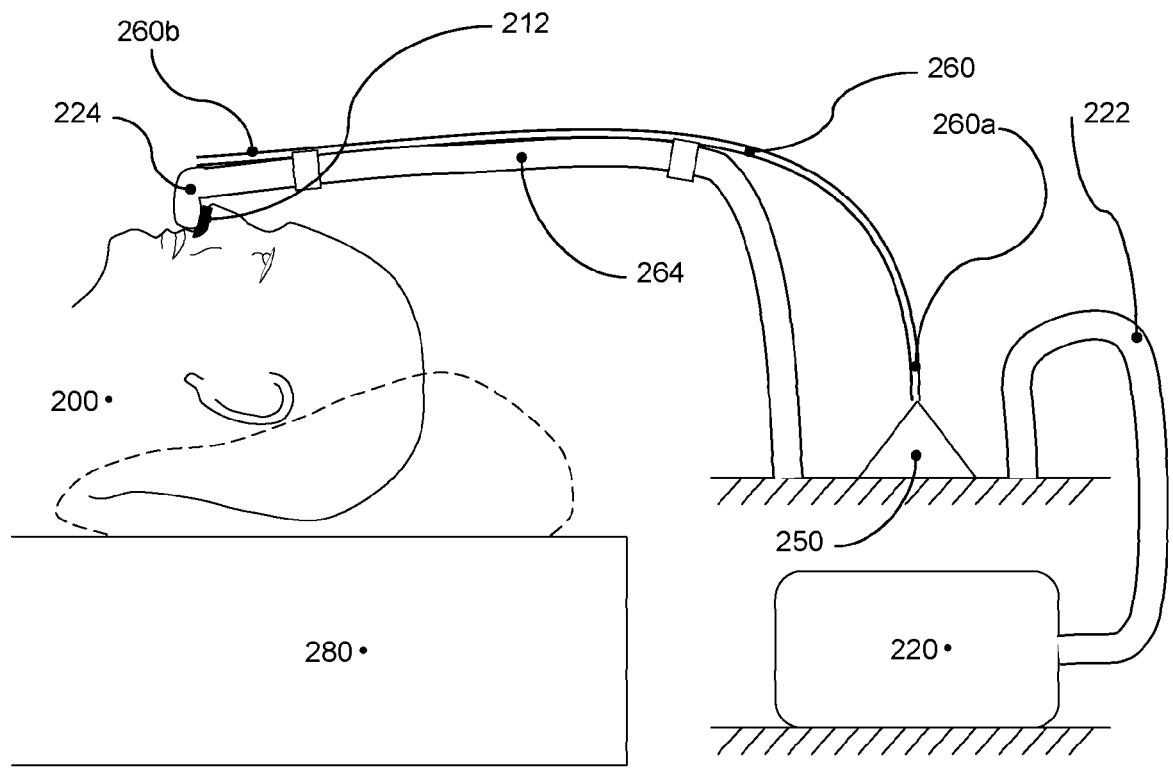
FIG. 5 depicts an embodiment of the present invention wherein a flexible support, extending from the base of the device to an interface, is used to maintain contact between a patient and an interface.

In a first embodiment of the present invention, shown in FIG. 5, the support extension 260 consists of a single member. This member is securely fastened at a first fixed end 260a to the base 250 of the support device. The second, free end 260b, of this member is connected to an interface 224 of the apparatus. The base 250 is fastened securely to a fixed point on the bed 280 of the patient, or another fixed location or object in the room, such as a wall or piece of furniture, in such a way as to prevent motion of any part of the base 250. Relative motion between the ends of the moveable support extension 260a and 260b is achieved by its own elastic deformation, and the resulting sealing pressure between the interface 224 and the face of the patient 200 occurs due to tension, compression, bending, or torsion of the support extension 260. The base 250 and support extension 260 are located away from the patient 200, such that only the sealing surface of the interface, depicted by the thickened line 212 in FIG. 5, comes into contact with the patient 200. In the preferred embodiment of the invention, the hose 222 supplying pressurized air from the PAP device 220 is connected to a point located on the base 250 of the subject device, thus eliminating leaks and discomfort caused by tugging of the hose 222 on the patient interface 224. An additional conduit 264 may be provided for the conveyance of treatment air between the point of attachment of the hose 222 to the base 250 and the interface 224 of the apparatus. Alternatively, the support extension 260 may be constructed with a hollow interior, provided for the conveyance of treatment air.

Figure 6A:
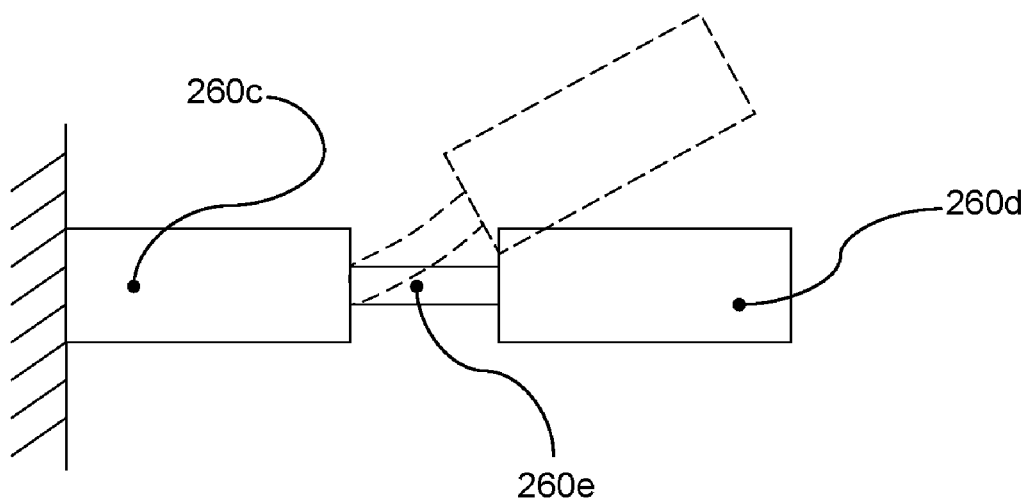
FIGS. 6a and 6b depict, schematically, two alternative means of achieving a range of motion through flexible support members.
Figure 6B:
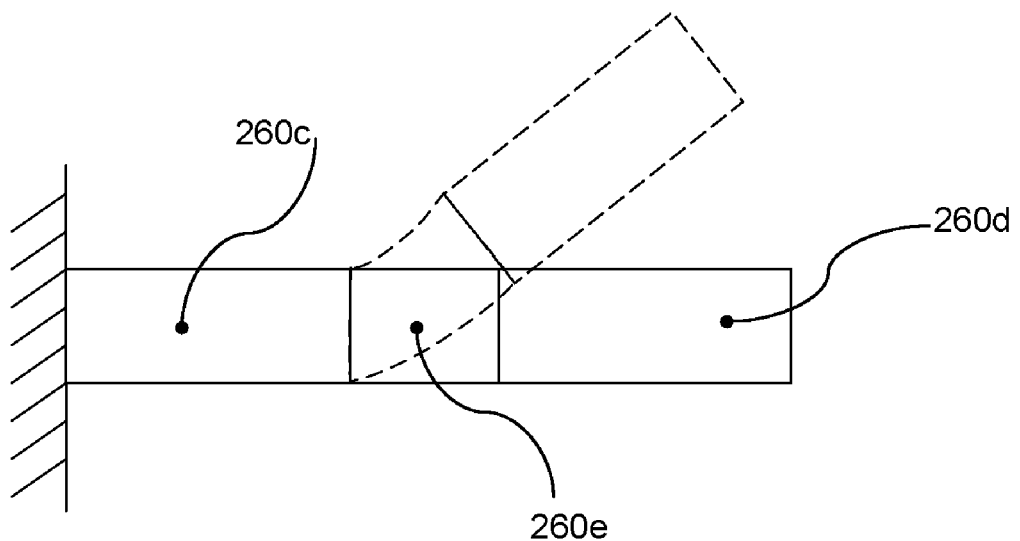

In one arrangement, the above-described support extension 260 may consist simply of a length of hose or tubing, preferably constructed of a pliable, elastic material, in order to provide both tension in, and motion of, the free end 260b of the support extension 260, and which also conveys treatment air directly from the PAP device 220, or from the hose 222 of the PAP device 220, to the interface 224 of the apparatus. However, to improve control of the tension and range of motion, the support extension member 260 may be constructed of a rigid material, and its stiffness to bending and torsion is adjusted locally along its length. This may be accomplished by varying the geometry and area of the cross-section, as shown in FIG. 6a, where bending motion, shown by the dashed lines, between two substantially rigid portions 260c and 260d of the member is permitted by reducing the cross-sectional area in a third intermediate region 260e. Bending may be allowed by constructing different sections of the arm from materials having substantially different mechanical properties, as shown in FIG. 6b, where two substantially rigid portions 260c and 260d of the member are joined by a section 260e having the same cross-section as sections 260c and 260d, but is constructed of a material having a substantially lesser resistance to deformation. A final alternative is to use a combination of these two methods, and vary both the material and the cross-section of the support extension along its length.

Figure 7:
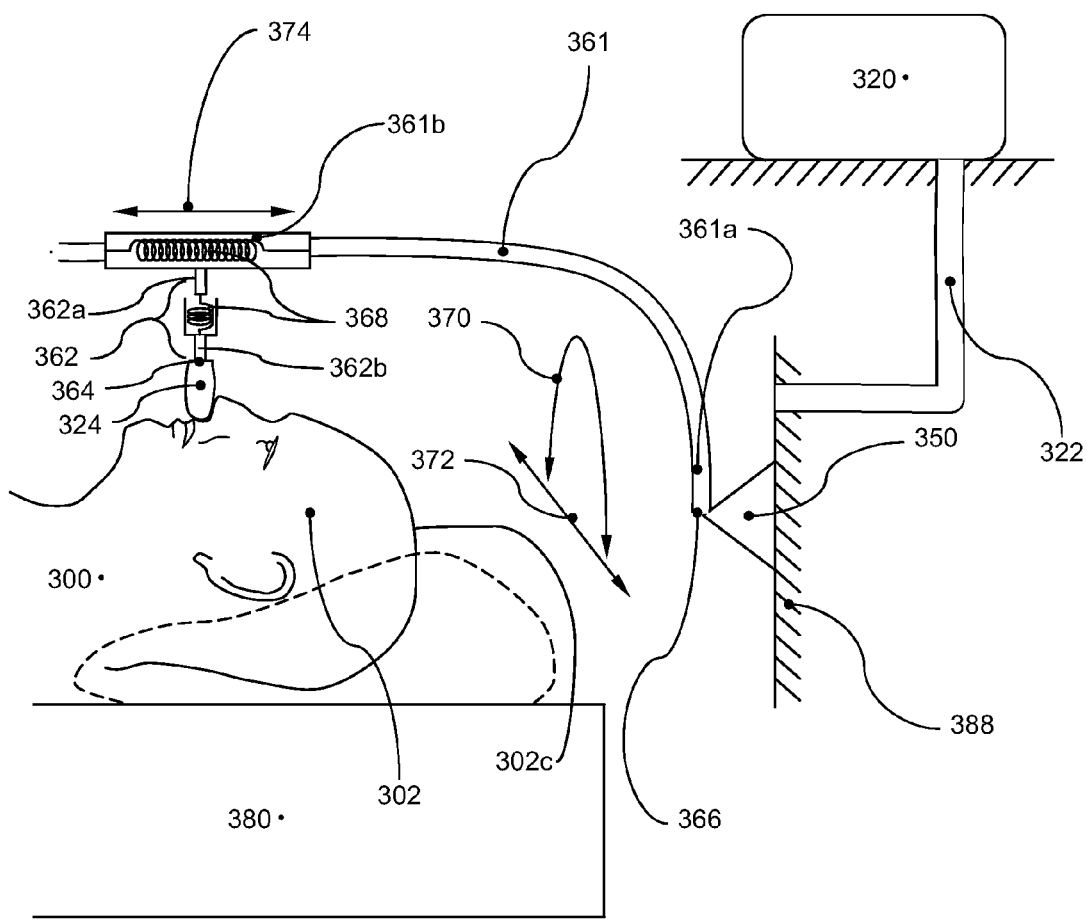
FIG. 7 depicts an embodiment of the present invention wherein a substantially horizontal and rigid support, rotatably coupled to the base of the device, and two sliding connections, are used to maintain contact between a patient and an interface.

In a second embodiment of the present invention, depicted in FIG. 7, the moveable support extension consists of a number of different rigid members. As in the previous embodiment, the support extension is attached at a first end to a rigid base 350 of the support device, and the second, free end is adapted to be coupled to a suitable interface 324 of the PAP device. The base 350 is fastened securely to a fixed point on the bed 380 of the patient, or another fixed location or object in the room, such as a wall or piece of furniture, in such a way as to prevent motion of either end of the base 350. The members of the moveable support extension may be interconnected by hinged, pinned, or other rotating joints, and sliding, telescoping, or other extending connections common in the art.

In the embodiment shown in FIG. 7, the moveable support extension consists of two moving, rigid members. The first member 361 has a first end 361a that is coupled to the base 350 of the apparatus, and a second end 361b that is coupled to a first end 362a of the second member 362. The second member 362 has a second end 362b adapted to be coupled to a suitable interface 324 of the PAP device by an interface mount 364. Rotation of the free end 362b of the moveable support extension about the longitudinal axis of the patient is intended to follow rolling motion of the patient 370. This motion is achieved by having the first end 361a of the first member 361 of the moveable support extension coupled to the base 350 by a rotatable connection 366 such as a hinge, rotating shaft, or a radial bushing or bearing. Longitudinal translation of the free end 361b, as depicted by the arrows 374 in FIG. 7, is also incorporated into the mechanism in order to follow upward/downward shifting of the patient 300. This is achieved by a longitudinal sliding connection between the two members 361 and 362 at their point of connection. Suitable sliding connections may consist of a piston and cylinder, a track and ball or roller, a sliding block and guide-rail, or any similar method common in the art. Automatic tracking of lateral translation (sideways shifting) of the patient is achieved by allowing radial telescoping of the second member 362 by any suitable means, such as a piston and cylinder, in addition to rolling 370, as described above.

As with the first embodiment of the present invention, the hose 322 supplying compressed air from the PAP device 320 may be attached directly to the interface 324 of the PAP device. However, in the preferred embodiment of FIG. 7, the hose 322 is attached at a point on the base 350 of the support device, and an additional conduit is provided (not shown in FIG. 7), having the same purpose, and similar design to that described in the embodiment of FIG. 5.

It is apparent from FIG. 7 that the required radial (or lateral) translation while tracking a patient undergoing a rolling motion is eliminated by having the axis of rotation of the moveable support extension about the base 350 collinear with an axis of rotation generally passing through the center of the patient 300. However, because a rolling 370 patient will also often simultaneously undergo a lateral translation 372, it is not always possible or convenient to maintain a collinear relationship between these two axes of rotation. The required radial (or lateral) translation is minimized however by placing the axis of rotation of the moveable support extension as closely as possible to the axis of rotation of the rolling patient. Thus, in the preferred embodiment of the present invention, the end of the base 350 to which the moveable support extension is fastened is located behind the head 302 of the patient (i.e. near the crown 302c) while in bed 380, at or near the same elevation as the central axis of the patient's body. In other words, the hinged connection 366 is placed between the head 302 of the patient and the headboard 388, if present, as depicted in the example of FIG. 7.

In the preferred embodiment, the moveable support extension comprises force-generating elements designed to provide sealing pressure between the interface and the patient. The forces produced by these elements are transmitted, through the elements of the moveable support extension, to the point 361a where the support extension attaches to the base 350 of the device. The elements 361 and 362 of the support extension are distanced from the patient 300, thereby limiting contact between the patient and the device to the sealing surface of the nasal, or oral-nasal, interface fitting 324. In FIG. 7 these force-generating elements consist of coil springs, which are represented in the schematic at 368, and which may be in tension or compression. The stiffness and pre-loading of each of these springs is chosen to provide an adequate range of motion, without excessive force being placed on the face of the patient. The pre-loading of the springs is ideally adjustable, such that the patient can vary the sealing pressure according to his or her need. However, the use of coil springs in this embodiment is by way of example only, and any number of force-generating members common in the art may be substituted. Examples include: leaf springs; spiral (torsion) springs; weights and pulleys; pneumatic and hydraulic elements; and rubbers and elastomeric materials. Additionally, active force-generating elements may also be used in situations where passive elements do not provide adequate control. Examples include: linear and rotary electric motors; servomechanisms; hydraulic or pneumatic actuators; piezoelectric elements; and shape-memory alloys.

As a further comfort-enhancing measure, the moveable support may incorporate buttons, knobs, or other control mechanisms, which are used to control certain functions of the positive airway pressure device. Such controls could include: powering the device on and off; adjusting the time required to reach full-pressure of the device (ramp time); and adjusting the level of humidification provided by the device.

As will be apparent to those skilled in the art, additional embodiments of the present invention are possible by blending the concepts provided in the above-described first and second embodiments. For example, any number of combinations of rigid and elastic members, which may or may not be in relative motion, may be used to construct the moveable support extension. Alternatively, allowing flexion or torsion of members in relative motion may provide additional control to account for patient motions not covered in the previous embodiments.

Each of the above embodiments of the moveable support extension can be used in conjunction with any number of means of attachment of the base of the device to a fixed point on the bed of the patient, or to another fixed location or object in the room. As was noted previously, the preferred point of attachment of the moveable support extension to the base is behind the head of the patient while lying in bed, at or near the same elevation as the central axis of the patient's body, as reflected in the following examples of embodiments of the base of the device.

Figure 8:
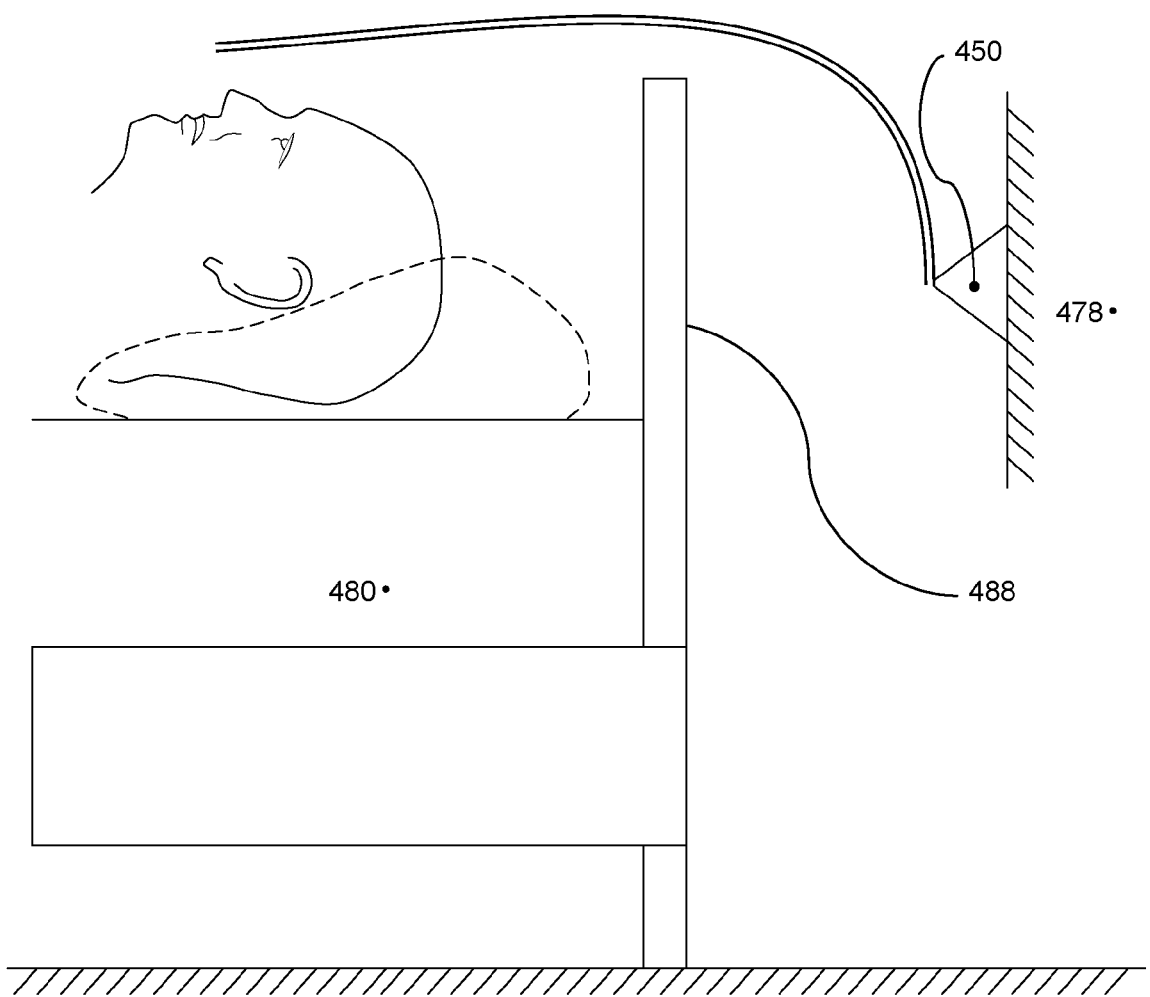
FIG. 8 depicts an embodiment of the base of the device wherein the base is rigidly secured to a wall of the room, a headboard of the bed, or another substantially immovable object or item of furniture in the room.

FIG. 8 depicts an embodiment of the base 450 of the present invention, in which the base 450 is attached to a wall 478 of the room. Alternatively, the base of this embodiment may be attached to a headboard 488 of the bed 480, if present, or some other object or piece of furniture in the room (not shown in the Figure). The base may be secured by any means common in the art, such as screws, nails, pins, tacks, hooks or hangers, adhesives, hook-and-loop materials (i.e. Velcro™), or suction cups.

Figure 9:
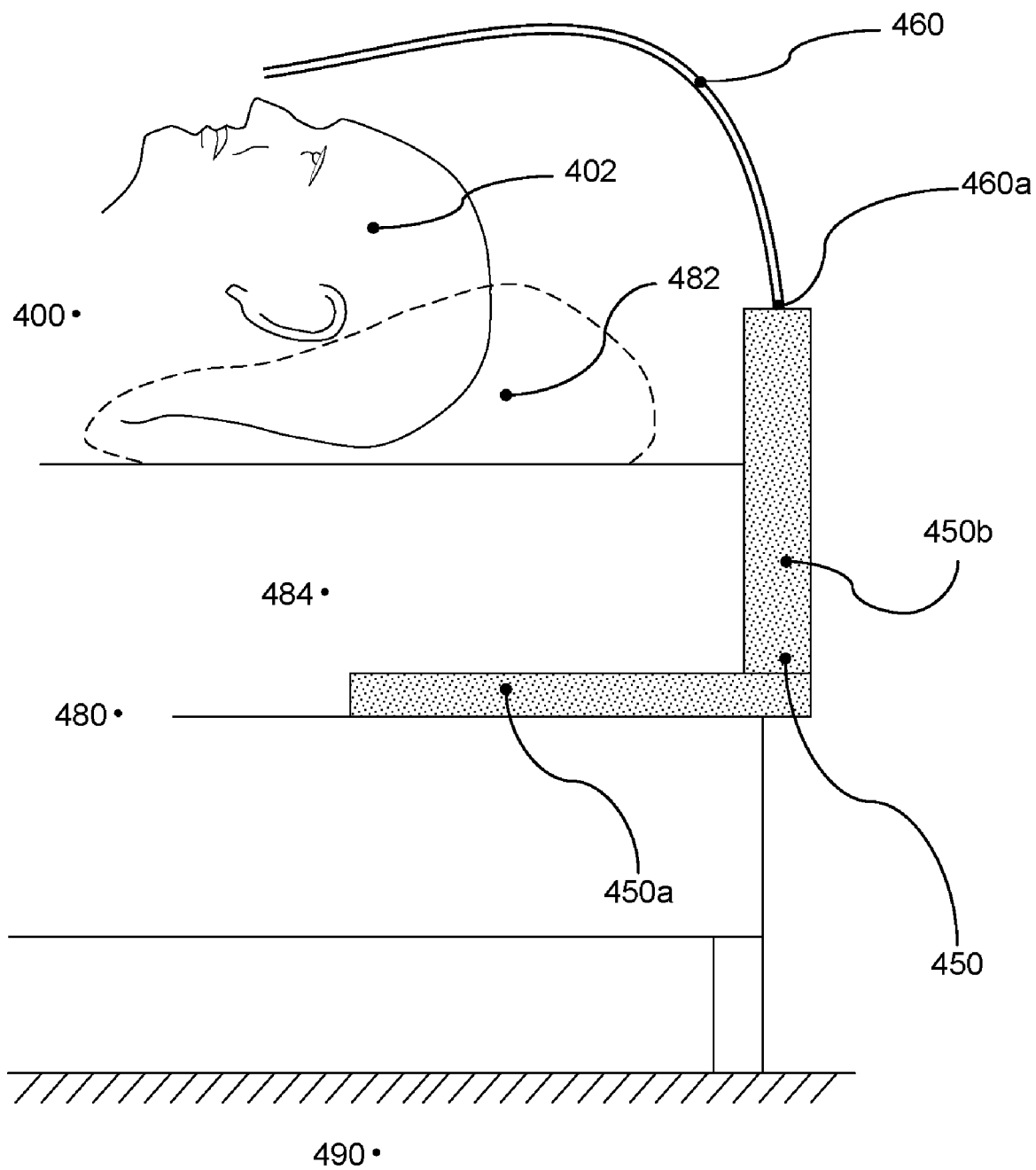
FIG. 9 depicts an embodiment of the present invention wherein the base of the device is constructed of horizontal and vertical portions, where the horizontal portion is designed to be placed under a mattress of the bed, under a pillow of the bed, or on the floor of the room; and, FIG. 10 depicts an embodiment of the present invention wherein the base of the device is incorporated into a pillow or a pillowcase of the patient.

Another embodiment of the base of the present invention is provided in FIG. 9. In this embodiment, the base 450 consists of a flat (horizontal) portion 450a, and a substantially vertical support 450b. The horizontal portion 450a of the base 450 may be secured by placing it under the mattress 484 of the bed 480, as shown in the embodiment of FIG. 9. In this embodiment, the weight of the mattress 484 and/or the patient 400 is used to maintain the position of the base 450. The vertical support 450b extends upwards behind the mattress 484 and/or headboard of the patient (not shown in figure), such that the point of attachment 460a of the support extension mechanism 460 may be located behind the patient's head 402, and the apparatus aligned or centered with the patient's body. For clarity, other accessories, such as the interface and hose(s) of the apparatus have been omitted from FIG. 9. Alternative means of securing the base include placement under the pillow 482 of the patient, or on the floor 490 of the room, which is easily achieved by varying the length of the vertical support 450b. The horizontal portion 450a of the base 450 may also be provided with additional means of restraining its motion. Examples include non-slip surfaces, hook and loop materials (Velcro™), or placing a heavy object on top of the horizontal portion of the base.

Figure 10:
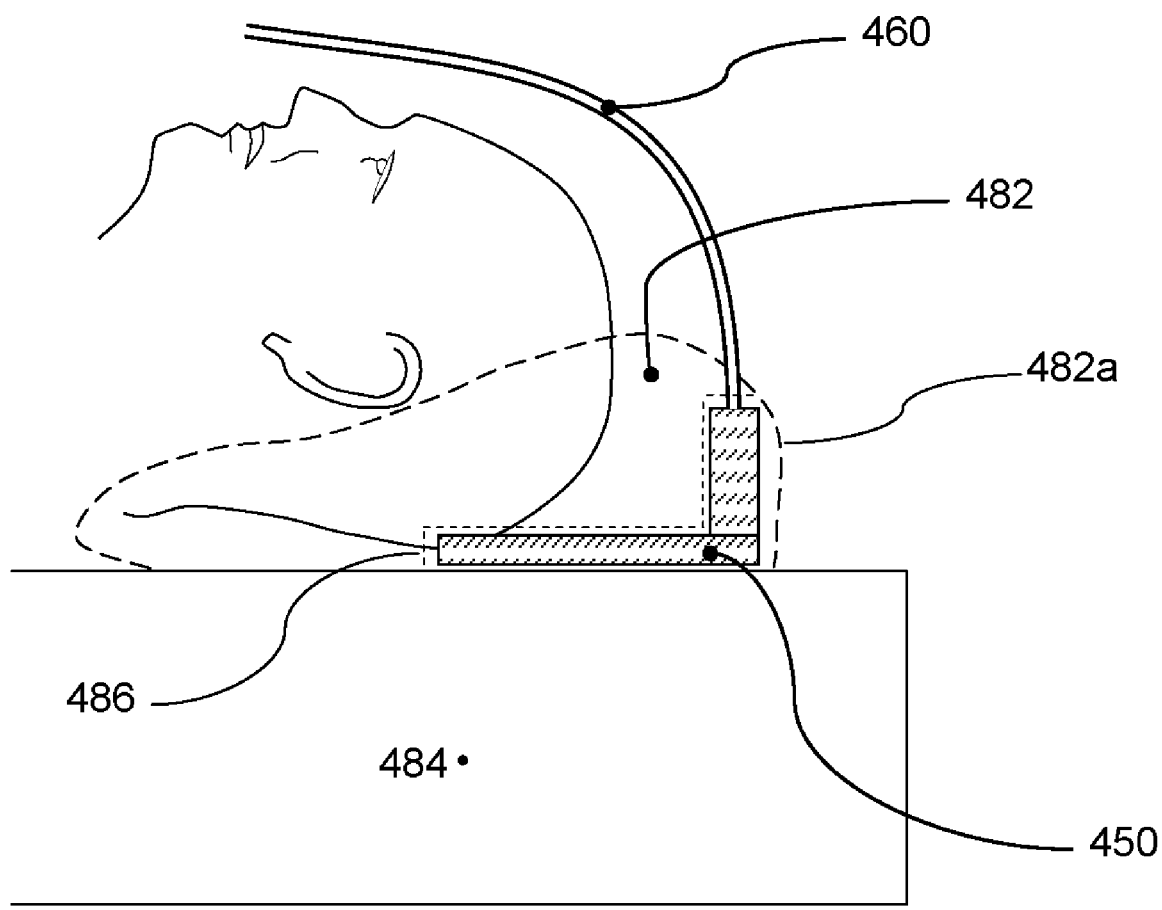

In yet another embodiment of the present invention, depicted in FIG. 10, the base 450 of the device is incorporated into a pillow 482 or pillowcase 482a of the patient. In this embodiment, a sleeve or pocket, represented by the dotted line 486, is provided in the pillow 482 or pillowcase 482a of the patient to which a suitably adapted portion of the base may be inserted. The pocket may be formed as an integral part of the pillow 482 or pillowcase 482a, or it may be attached by some other temporary or removable means, such as with conventional buttons, snap-buttons, a zipper, or a hook-and-loop (Velcro™) material. The preferred embodiment is adapted to provide a sleeve 486 or other means of attachment of the base 450 extending both behind and underneath the pillow 482 of the patient, to provide maximum stability of the base 450. The sleeve 486 may also be adapted to further incorporate a PAP device into the pillow 486 or pillowcase 486a.

It is understood that in all of the above embodiments of the base of the device, the base may be constructed of a single part, or it may consist of several parts that are rigidly secured together.

The present invention is intended primarily for use in conjunction with positive airway pressure devices used in the treatment of obstructive sleep apnea. However, numerous medical conditions exist for which treatment comprises delivery of a gas to the airway of a patient, and for which a patient interface support device is required. Upon examination of the various embodiments of the present invention disclosed herein, those ordinarily skilled in the art will recognize that the present invention may also be easily adapted to support other devices, such as a cannulae used in treatments involving delivery of a compressed gas.

What is claimed is:

1. A patient interface support for a Positive Airway Pressure (PAP) device, the device including a pressurized air source, a patient interface for supplying air to a patient's airflow passages and an air supply conduit for supplying pressurized air from the pressurized air source to said patient interface, said patient interface support comprising:
   a base for attachment to a support surface;
   a support extension including a first member and a second member, said first member having a joint for moveably connecting said support extension to said base at one end of said first member;
   said second member having a first end and a second end, said first end slidably coupled to an opposite end of said first member with a sliding connection along a longitudinal axis of the first member, the sliding connection being a piston and a cylinder, a track and ball or roller, or a sliding block and guide rail;
   a patient interface mount for mounting the patient interface at said second end of said second member; and
   biasing means in said support extension to apply a pre-selected engagement pressure at said patient interface to create a seal between said patient interface and the patient's airflow passages when said patient interface support is in use, wherein said seal between said patient interface and the patient's airflow passages is the only contact between the patient and said patient interface and the pre-selected engagement pressure being generated by coil springs, spiral or torsion springs, weights and pulleys, pneumatic or hydraulic elements, rubbers and elastomeric materials, linear and rotary motors, servomechanisms, hydraulic or pneumatic actuators, piezoelectric elements, or shape memory alloys.

2. The patient interface support of claim 1, wherein said support extension has a support arm extending from said joint to said patient interface mount and said biasing means is at least one elastic portion in said support arm.

3. The patient interface support of claim 2, wherein the seal between said patient interface and the patient's airflow passages is maintained by pressure generated by the deformation of said elastic portion in said support arm.

4. The patient interface support of claim 2, wherein whole of said support arm is elastic.

5. The patient interface support of claim 2, wherein said support arm has at least two rigid portions and said biasing means is an elastic portion connecting said rigid portions.

6. The patient interface support of claim 5, wherein said elastic portion has a cross-sectional area smaller than that of said rigid portions.

7. The patient interface support of claim 2, wherein said air supply conduit of the PAP device is connected to said base and a second air supply conduit conveys air from said base to said patient interface.

8. The patient interface support of claim 7, wherein said support arm has a hollow interior for conveyance of air from said base to said patient interface.

9. The patient interface support of claim 1, wherein said biasing means is at least one spring loaded portion.

10. The patient interface support of claim 1, wherein said support extension follows the motion of the patient.

11. The patient interface support of claim 1, wherein control means are provided in said support extension in the vicinity of the patient for controlling the PAP device.

12. The patient interface support of claim 1, wherein said base is attached to said support surface by means of screws, nails, pins, tacks, hooks, hangers, adhesives, hook-and-loop materials, suction cups, or combinations thereof.

13. The patient interface support of claim 1, wherein said base comprises of a substantially horizontal base portion and a substantially vertical support portion.

14. The patient interface support of claim 1, wherein said base is incorporated into a pillow or a pillowcase of the patient.

15. A patient interface support kit for a Positive Airway Pressure (PAP) device, the device including a pressurized air source, a patient interface for supplying air to a patient's airflow passages and an air supply conduit for supplying pressurized air from the pressurized air source to said patient interface, said patient interface support kit comprising:
- a base for attachment to a support surface; and
- a support extension including a first member and a second member, said first member having a joint; a patient interface mount; and a biasing means;
- said joint for moveably connecting said support extension to said base at one end of said first member, said second member having a first end and a second end, said first end slidably coupled to an opposite end of said first member with a sliding connection along a longitudinal axis of the first member, the sliding connection being a piston and a cylinder, a track and ball or roller, or a sliding block and guide rail, said patient interface mount for supporting said patient interface at said second end of said second member, and said biasing means for applying a pre-selected engagement pressure at said patient interface to create a seal between said patient interface and the patient's airflow passages when said patient interface support is in use, wherein said seal between said patient interface and the patient's airflow passages is the only contact between the patient and said patient interface and the pre-selected engagement pressure being generated by coil springs, spiral or torsion springs, weights and pulleys, pneumatic or hydraulic elements, rubbers and elastomeric materials, linear and rotary motors, servomechanisms, hydraulic or pneumatic actuators, piezoelectric elements, or shape memory alloys.

* * * * *